United States Patent [19]
Audousset et al.

[11] Patent Number: 5,693,101
[45] Date of Patent: Dec. 2, 1997

[54] COMPOSITION FOR THE OXIDATION DYEING OF KERATINOUS FIBRES COMPRISING A 3-FLUOROPARA-AMINOPHENOL AND AT LEAST ONE COUPLER SELECTED FROM A META-AMINOPHENOL AND A META-PHENYLENEDIAMINE AND DYEING PROCESS USING SUCH A COMPOSITION

[75] Inventors: Marie-Pascale Audousset, Asnieres; Jean Cotteret, Verneuil S/Seine, both of France

[73] Assignee: L'Oreal, Paris, France

[21] Appl. No.: 640,057

[22] Filed: Apr. 30, 1996

Related U.S. Application Data

[63] Continuation of Ser. No. 357,022, Dec. 16, 1994, abandoned.

[30] Foreign Application Priority Data

Dec. 22, 1993 [FR] France .................................. 93 15486

[51] Int. Cl.$^6$ ...................................................... A61K 7/13
[52] U.S. Cl. ........................... 8/408; 8/406; 8/416; 8/421; 8/615
[58] Field of Search ................................ 8/405, 406, 408, 8/410, 411, 412, 421, 615

[56] References Cited

U.S. PATENT DOCUMENTS

| | | | |
|---|---|---|---|
| 3,210,252 | 10/1965 | Blanke et al. | 167/88 |
| 3,918,896 | 11/1975 | Kalopissis et al. | 8/412 |
| 4,065,255 | 12/1977 | Andrillon et al. | 8/412 |
| 4,217,914 | 8/1980 | Jacquet et al. | 8/426 |
| 4,333,730 | 6/1982 | Bugaut et al. | 8/408 |
| 4,420,637 | 12/1983 | Bugaut et al. | 8/407 |
| 4,422,853 | 12/1983 | Jacquet et al. | 8/406 |
| 4,948,579 | 8/1990 | Jacquet et al. | 424/70 |
| 5,196,189 | 3/1993 | Jacquet et al. | 424/72 |

FOREIGN PATENT DOCUMENTS

| | | |
|---|---|---|
| A 1472078 | 4/1965 | France . |
| A-2270846 | 12/1975 | France . |
| 2421870 | 12/1979 | France . |
| A-1048790 | 11/1966 | United Kingdom . |
| 1597034 | 9/1981 | United Kingdom . |

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

An oxidation dyeing composition for keratinous fibers, in particular for human keratinous fibers such as hair, of the type comprising, in a medium appropriate for dyeing, at least one oxidation dye precursor, the oxidation dye precursor being 3-fluoro-para-aminophenol or one of its acid addition salts, and at least one coupler selected from a meta-aminophenol and a meta-phenylenediamine. The use of this composition in a process for dyeing keratinous fibers, especially hair, is also disclosed.

27 Claims, No Drawings

COMPOSITION FOR THE OXIDATION DYEING OF KERATINOUS FIBRES COMPRISING A 3-FLUOROPARA-AMINOPHENOL AND AT LEAST ONE COUPLER SELECTED FROM A META-AMINOPHENOL AND A META-PHENYLENEDIAMINE AND DYEING PROCESS USING SUCH A COMPOSITION

This application is a continuation of application Ser. No. 08/357,022 filed Dec. 16, 1994, now abandoned.

The present invention is directed to a composition for the oxidation dyeing of keratinous fibres, in particular human keratinous fibres, comprising at least one 3-fluoro-para-aminophenol in combination with at least one coupler of the meta-aminophenol or meta-phenylenediamine type of formula (I), described below.

It is known to dye keratinous fibres, and in particular human keratinous fibres such as hair, with dyeing compositions containing oxidation dye precursors, in particular ortho- or para-phenylenediamines or ortho- or para-aminophenols, generally known as "oxidation bases," and couplers, also known as colouring modifiers, more particularly meta-phenylenediamines, meta-aminophenols and meta-diphenols, which make it possible to modify and enrich with highlights the "foundation" colourings obtained with the condensation products of oxidation bases.

A strong craze for colourings with coppery, mahogany or red highlights is currently observable. Thus far, these shades have been obtained with dyes based on para-aminophenol in combination with specific couplers. However, the use of para-aminophenol is currently being questioned for toxicological reasons.

Substitution of para-aminophenol is all the more problematic since, in order to be entirely satisfactory, the dyes must also be resistant to light, to washes, to bad weather, to perspiration and to the various treatments to which hair may be subjected.

It has been proposed to replace para-aminophenol by using 3-methyl-para-aminophenol, such as has been described in U.S. Pat. No. 3,210,252, the disclosure of which is incorporated by reference. This product is nevertheless insufficiently soluble in dyeing media, leads to recrystallization in the compositions and, finally, does not make it possible to obtain the desired coppery shades.

It is known, moreover, according to French Patent No. 1,472,078, the disclosure of which is incorporated by reference, to carry out oxidation dyeings with 3-fluoro-para-aminophenol. However, the shades obtained with 3-fluoro-para-aminophenol are yellow and do not lead to shades with coppery, mahogany or red highlights.

After much research, it has been discovered that by combining 3-fluoro-para-aminophenol with couplers of formula (I), discussed in the following text, it is possible to obtain shades with copper, mahogany or red highlights which are intense and which satisfy the resistance criteria discussed above, while avoiding the problems encountered with para-aminophenol and its 3-methylated derivative, especially the problems of toxicology and recrystallization.

The subject of the present invention is thus an oxidation dyeing composition for keratinous fibres, in particular for human keratinous fibres such as hair, comprising, in a medium appropriate for dyeing,
at least one oxidation dye precursor, at least one of the precursors, being 3-fluoro-para-aminophenol or an acid addition salt thereof; and
at least one coupler compound of formula (I):

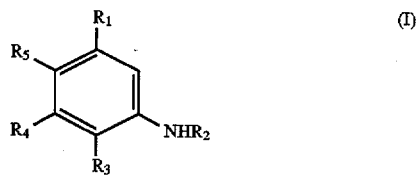

in which $R_1$ represents an amino or hydroxyl radical, such that:

when $R_1$ represents an amino radical, $R_2$ represents a hydrogen atom, an alkyl or a mono- or polyhydroxyalkyl radical; $R_3$ represents a hydrogen atom, an alkyl or a monohydroxyalkoxy radical; $R_4$ represents a hydrogen atom or an alkyl radical; and $R_5$ represents an alkoxy, an aminoalkoxy, a mono- or polyhydroxyalkoxy radical or a 2,4-diaminophenoxyalkoxy radical;

when $R_1$ represents a hydroxyl radical, $R_2$ represents a hydrogen atom, an alkyl or a mono- or polyhydroxyalkyl radical; $R_3$ represents a hydrogen atom, an alkyl, an alkoxy radical or a halogen atom; $R_4$ represents a hydrogen atom; and $R_5$ represents a hydrogen atom, an alkyl, an alkoxy, a mono- or polyhydroxyalkyl or a mono- or polyhydroxyalkoxy radical; and further in which the alkyl or alkoxy radicals may contain from 1 to 4 carbon atoms; the mono- or polyhydroxyalkyl and mono- or polyhydroxyalkoxy radicals may represent alkyl or alkoxy radicals which may contain from 2 to 3 carbon atoms and from 1 to 3 hydroxyl groups; and the halogen atom may be selected from chlorine, fluorine or bromine atoms;

or an acid addition salt thereof.

The present invention also contemplates a process for dyeing keratinous fibres, and in particular human keratinous fibres such as hair, which comprises the steps of:

(i) applying to the fibres the dyeing composition as described above; and (ii) using an oxidizing agent, the oxidizing agent being applied to the fibres simultaneously with or subsequent to the dyeing composition, to develop the colour of the dyeing composition in an acidic, neutral or alkaline medium.

Another subject of the present invention is a dyeing device or "kit" comprising at least two compartments, one of the compartments containing a dyeing composition as described above, and another of the compartments containing a composition (B) containing an oxidizing agent in a medium appropriate for dyeing.

The present invention further contemplates a process for dyeing keratinous fibres, and in particular human keratinous fibres such as hair, which comprises the steps of:

(i) applying to the fibres a dyeing composition as described above, the dyeing composition being obtained from a kit for dyeing keratinous fibres comprising at least two compartments, one of the compartments containing a dyeing composition and another of the compartments containing a composition (B) containing an oxidizing agent in a medium appropriate for dyeing; and (ii) using the oxidizing agent and the appropriate dyeing medium, the agent and the medium being applied to the fibres simultaneously with or subsequent to the dyeing composition to develop the colour of the dyeing composition in the medium.

The present invention is also directed to a ready-to-use dyeing composition, comprising the various agents used for dyeing keratinous fibres, and in particular for dyeing human keratinous fibres such as hair, as described above, and an oxidizing agent, in a neutral, alkaline or acidic medium preferably having a pH ranging from 3 to 11.

The dyeing compositions according to the invention, which are moreover non-allergizing dyes, make it possible to obtain shades with coppery, mahogany or red highlights which are intense and which are remarkably resistant to light, to washes, to bad weather and to the various treatments to which hair may be subjected. The dyeing composition according to the invention are particularly very resistant to perspiration.

Other subjects of the present invention will become apparent upon reading the description below and the examples which follow.

The acid salts that may be used according to the invention are preferably chosen from hydrochlorides, sulphates, hydrobromides and tartrates.

3-Fluoro-para-aminophenol and its acid addition salts may be present in proportions ranging from approximately 0.005% to 3% by weight with respect to the total weight of the dyeing composition and preferably ranging from approximately 0.05% to 2%.

Preference is given, among the couplers of formula (I), to meta-aminophenols chosen from 5-amino-1-hydroxy-2-methoxybenzene, 5-amino-1-hydroxy-2-(β-hydroxyethyloxy) benzene, 1-hydroxy-5-(β-hydroxyethylamino)-4-methoxy-2-methylbenzene, 5-amino-1-hydroxy-4-methoxy-2-methylbenzene, 5-amino-4-chloro-1-hydroxy-2-methylbenzene, 5-amino-2,4-dimethoxyphenol and 1-hydroxy-5-(γ-hydroxypropylamino)-2-methylbenzene, and to meta-phenylenediamines chosen from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, 1,3-bis(2,4-diaminophenoxy) methane, 1-(β-aminoethyloxy)-2,4-diaminobenzene, 2-amino-1-(β-hydroxyethyloxy)-4-(methylamino)benzene, 1,3-diamino-4,6-bis(β-hydroxyethyloxy)benzene, 2,4-diamino-1-ethoxy-5-methylbenzene, 2,4-diamino-5-(β-hydroxyethyloxy)-1-methylbenzene and 2,4-diamino-1-(β, γ-dihydroxypropyloxy)benzene.

More preferably used are the compounds of formula (I) in which $R_3$ and $R_4$ represent a hydrogen atom and particularly meta-aminophenols such as 5-(β-hydroxyethylamino)-2-methylphenol and 5-amino-2-methylphenol and meta-phenylenediamines such as 2,4-diamino-1-(β-hydroxyethyloxy)benzene and 2-amino-4-(β-hydroxyethylamino)-1-methoxybenzene.

These couplers of formula (I) and their acid addition salts may be present in proportions ranging from approximately 0.001% to 3% by weight with respect to the total weight of the dyeing composition and preferably ranging from approximately 0.05% to 2%.

The combination of 3-fluoro-para-aminophenol and coupler(s) of formula (I) represents from approximately 0.006% to 5% by weight, and preferably from approximately 0.1% to 3% by weight, with respect to the total weight of the composition.

The oxidizing agent is preferably chosen from hydrogen peroxide, urea hydrogen peroxide, alkali metal bromates and persalts such as perborates and persulphates. Hydrogen peroxide is particularly preferred. The concentration of hydrogen peroxide may range from 1 to 20 volumes, i.e., from 0.3% to 6% by weight relative to the total weight of the composition, and preferably ranges from 1 to 10 volumes, i.e., from 0.3% to 3% by weight relative to the total weight of the composition.

The composition (A), which contains the combination of the dyes as described above, preferably has a pH ranging from 3 to 10.5. The pH can be adjusted to the desired value by means of either basifying agents commonly used in dyeing keratinous fibres, such as aqueous ammonia, alkali metal carbonates, alkanolamines such as, for example, mono-, di- and triethanolamines and their derivatives, sodium or potassium hydroxide or the compounds of formula (II):

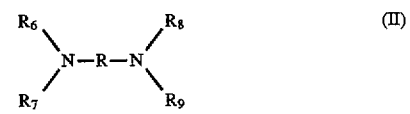

in which R is a propylene residue optionally substituted by a hydroxyl group or a $C_1$-$C_4$ alkyl radical, and $R_6$, $R_7$, $R_8$ and $R_9$, simultaneously or independently of one another represent a hydrogen atom, a $C_1$-$C_4$ alkyl or $C_1$-$C_4$ hydroxyalkyl radical, or by means of conventional acidifying agents, such as inorganic or organic acids such as, for example, hydrochloric, tartaric, citric and phosphoric acids.

The pH of the composition (B) containing the oxidizing agent as defined above, is such that, after mixing with the composition (A), the pH of the composition applied to the keratinous fibres, preferably human keratinous fibres, preferably ranges from 3 to 11. The pH can be adjusted to the desired value using well-known acidifying, or optionally basifying, agents such as those described above. The oxidizing composition (B) preferably contains a hydrogen peroxide solution.

According to a preferred embodiment of the dyeing process of the invention, the dyeing composition (A) described above is mixed, at the time of use, with an oxidizing solution in an amount sufficient to develop a colouring. The mixture obtained is applied to keratinous fibres, preferably human keratinous fibres, and left exposed for a time period ranging from 5 to 40 minutes, preferably from 15 to 30 minutes, after which the fibres are rinsed, washed with a shampoo, rinsed again and dried.

The dyeing compositions of the present invention can also contain, in addition to the dyes discussed above, other couplers and/or direct dyes, particularly for modifying the shades or for enriching the shades with highlights, as well as oxidation bases other than 3-fluoro-para-aminophenol.

These couplers are well known in the art and may be chosen from meta-diphenols, hydroxylated naphthalene derivatives, sesamol derivatives, aminated or hydroxylated benzomorpholine derivatives, 2,6-diaminopyridine or its derivatives, hydroxyindoles, including particularly 6-hydroxyindole and aminoindoles.

The other oxidation bases can be chosen from para-phenylenediamines, among which there may preferably be mentioned para-phenylenediamine, paratoluytenediamine, 2,6-dimethyl-para-phenylenediamine, 2-hydroxymethyl-para-phenylenediamine, 2-(β-hydroxyethyl)-para-phenylenediamine, 2-(n-propyl)-para-phenylenediamine, 2-isopropyl-para-phenylenediamine, N-(β-hydroxypropyl)-para-phenylenediamine, N,N-di(β-hydroxyethyl)-para-phenylenediamine and 4-amino-N-(β-methoxyethyl)aniline, ortho-aminophenols and heterocyclic bases, such as 2,4,5, 6-tetraamino-pyrimidine and 2,5-diaminopyridine.

The direct dyes are preferably chosen from azo or anthraquinone dyes or nitro derivatives of the benzene series.

The dyeing compositions may also contain, in a preferred embodiment, well-known anionic, cationic, non-ionic or amphoteric surface-active agents of the state of the art, or mixtures thereof, in proportions ranging from approximately 0.5% and 55% by weight, and preferably from approximately 2% and 50% by weight, with respect to the total weight of the composition.

The dyeing compositions may also contain organic solvents. Mention may be made among them, as examples, of lower $C_1$–$C_4$ alkanols, such as ethanol and isopropanol, glycerol, glycols or glycol ethers such as 2-butoxyethanol, propylene glycol and the monoethyl ether and monomethyl ether of diethylene glycol, and aromatic alcohols such as benzyl alcohol or phenoxyethanol, analogous products and their mixtures. These solvents are preferably present in proportions ranging from approximately 1% to 40% by weight, and more preferably from approximately 5% to 30% by weight, with respect to the total weight of the composition.

It is also possible to add thickening agents chosen, for example, from sodium alginate, gum arabic, optionally cross-linked acrylic acid polymers, cellulose derivatives and biopolysaccharides such as xanthan gum or inorganic thickening agents such as bentonite, preferably present in proportions ranging from approximately 0.1% and 5%, and more preferably ranging from approximately 0.2% to 3%, by weight with respect to the total weight of the composition.

Anti-oxidizing agents can also be introduced. They are chosen preferably from sodium sulphite, thioglycolic acid, thiolactic acid, sodium bisulphite, dehydroascorbic acid, hydroquinone, 2-methylhydroquinone, tert-butylhydroquinone and homogentisic acid and are present in proportions ranging from approximately 0.05% to 1.5% by weight with respect to the total weight of the composition.

The dyeing compositions can also contain other cosmetically acceptable adjuvants such as, for example, penetrating agents, sequestering agents, fragrances, buffers, dispersing agents, treating agents, conditioning agents, film-forming agents, preserving agents and opacifying agents.

The composition applied to the keratinous fibres, particularly human keratinous fibres such as hair, can be provided in various forms, such as in liquid, cream or gel form or in any other form appropriate for carrying out dyeing of keratinous fibres and especially of human hair. The composition can be packaged under pressure in an aerosol canister in the presence of a propellant and can form a foam.

Concrete examples illustrating the invention will now be given. The first step will be to define the tests used to evaluate the performances of the oxidation dyes according to the invention with regard to their resistance to perspiration, to light and to shampoos.

Resistance to Perspiration:

Use was made of a synthetic sweat solution of the following composition: 10 g of NACl, 1 g of potassium hydrogenphosphate, 0.25 g of histidine, lactic acid to pH=3.2 and distilled water to make up a total of 100 g. The locks of dyed hair were immersed in a crystallizing dish covered with a watch glass which contained this sweat solution and were left to stand for a time period ranging from 20 to 50 hours at 37° C. The locks were then rinsed and dried.

Resistance to Light (Xenotest):

Dyed hair was fixed to a support (cardboard or plastic). These supports were arranged on sample holders which rotated around a Xenon lamp for a period of time ranging from 20 to 80 hours at a degree of humidity ranging from 25 to 75% RH (Relative Humidity) and at a temperature of 25° C.

Resistance to Shampoos (Ahiba-Texomet Machine):

Locks of dyed hair were placed in a basket which was immersed in a solution of a standard shampoo. The basket was subjected to a vertical to-and-fro movement of variable frequency and to a rotational movement which reproduced the action of manual rubbing, which generated the formation of foam.

After being treated for 3 minutes, the locks were removed, rinsed and then dried. The dyed locks could be subjected to a number of consecutive shampoo tests.

EXAMPLE 1

The following dyeing composition was prepared:

| | |
|---|---|
| 3-Fluoro-para-aminophenol | 0.635 g |
| 5-(β-Hydroxyethylamino)-2-methylphenol | 1.25 g |
| para-Phenylenediamine | 0.27 g |
| Oleyl alcohol polyglycerolated with 2 mol of glycerol | 4.0 g |
| Oleyl alcohol polyglycerolated with 4 mol of glycerol, containing 78% of AM | 5.0 g AM |
| Oleic acid | 3.0 g |
| Oleylamine containing 2 mol of ethylene oxide, sold under the name Ethomeen O12 by the company Akzo | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulphite as an aqueous solution containing 35% of AM | 0.4 g AM |
| Ammonium acetate | 0.8 g |
| Anti-oxidizing agent, sequestering agent | q.s. |
| Fragrance, preserving agent | q.s. |
| Aqueous ammonia containing 20% of $NH_3$ | 10.0 g |
| Deminerlized water | q.s. for 100 g |

At the time of use, this composition was mixed, weight for weight, with hydrogen peroxide assaying at 20 volumes (6% by weight), which had a pH of 3.

A mixture was obtained which had a pH of 9.8.

This mixture was applied to natural or permed grey hair which contained 90% of white hairs for 30 minutes. After rinsing, washing with a shampoo, rinsing again and drying, the hair was dyed a coppery-red shade.

This shade, expressed as Munsell value, was the following:

on natural hair: 1.5 Y 2.9/3.0 on permed hair: 9.65 R 2.4/3.5

This dye had excellent resistance to perspiration, to light and to repeated shampoos.

Thus, in comparison with a dyeing of equivalent shade obtained with a dyeing composition analogous to that described above but in which 3-fluoro-para-aminophenol was substituted by para-aminophenol in an equimolecular amount, i.e., 0.54 g, the following deteriorations were obtained over the three resistance tests described above; these deteriorations are expressed as SE (Nickerson index) (the lower this index, the higher the resistance):

| | | Resistance (Nickerson index) | | |
|---|---|---|---|---|
| Dyeing composition with | Nature of the hair | to perspiration | to light (40 hours) | to 8 shampoos |
| 3-Fluoro-para-aminophenol | Natural | 2.1 | 3.7 | 6.7 |
| 3-fluoro-para-aminophenol | Permed | 3.1 | 3.5 | 17.5 |
| para-Aminophenol | Natural | 9.7 | 5.3 | 8.9 |
| para-Aminophenol | Permed | 6.5 | 5.8 | 23.0 |

A marked improvement in the resistance to perspiration, to light and to shampoos was thus observed for the dyeing carried out by means of the composition according to the invention.

EXAMPLES 2 TO 5

The following dyeing compositions in accordance with the invention are prepared:

| Dyes (See Table I) | x g |
|---|---|
| Oleyl alcohol polyglycerolated with 2 mol of glycerol | 4.0 g |
| Oleyl alcohol polyglycerolated with 4 mol of glycerol (78% of AM) | 5.7 g AM |
| Oleic acid | 3.0 g |
| Oleylamine containing 2 mol of ethylene oxide, sold under the name Ethomeen 012 by the Company Akzo | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulphite as an aqueous solution containing 35% of AM | 0.46 g AM |
| Ammonium acetate | 0.8 g |
| Anti-oxidizing agent, sequestering agent | q.s. |
| Fragrance, preserving agent | q.s. |
| Aqueous ammnonia containing 20% of $NH_3$ | 10.0 g |
| Demineralized water | q.s. for 100 g |

At the time of use, this composition is mixed, weight for weight, with hydrogen peroxide assaying at 20 volumes (6% by weight), with a pH of 3.

A mixture is obtained with a pH of 9.8.

This mixture is applied to natural or permed grey hair containing 90% of white hairs for 30 minutes. After rinsing, washing with a shampoo, rinsing again and drying, the hair is dyed the shades indicated in Table II below.

TABLE I

| Examples Dyes (in g) | 2 | 3 | 4 | 5 |
|---|---|---|---|---|
| 3-Fluoro-para-aminophenol | 0.381 | 0.381 | 0.381 | 0.7 |
| 5-Amino-2-methylphenol | 0.369 | | | |
| 2-Amino-4-(β-hydroxyethyl-amino)-1-methoxybenzene | | 0.765 | | |
| 2,4-Diamino-1-(β-hydroxy-ethyloxy)benzene dihydrochloride | | | 0.723 | |
| 5-(β-Hydroxyethylamino)-2-methylphenol | | | | 0.5 |
| 6-Hydroxyindole | | | | 0.4 |

TABLE II

| SHADES OBTAINED | EXAMPLES | | | |
|---|---|---|---|---|
| | 2 | 3 | 4 | 5 |
| Natural grey hair containing 90% of white hairs | Coppery dark blond | | mahogany chestnut | Coppery golden blond |
| Permed grey hair containing 90% of white hairs | Intense coppery light brown | Iridescent mahogany dark brown | mahogany chestnut | Coppery |

The inventors believe that the shades that would be obtained, as shown in Table II, should have resistance to perspiration, to light and to shampoos that is comparable with that obtained by the composition of Example 1 in accordance with the invention.

EXAMPLE 6

A following dyeing composition is prepared:

| 3-Fluoro-para-aminophenol | 0.6 g |
|---|---|
| 2-Aminophenol | 0.1 g |
| 5-Amino-2-methylphenol | 0.15 g |
| 5-(β-Hydroxyethylamino)-2-methylphenol | .77 g |
| Cetylstearyl alcohol (50/50 $C_{16}/C_{18}$), sold under the name Cire de Lanette O by the company Henkel | 18 g |
| 2-Octyldodecanol | 3 g |
| Cetylstearyl alcohol (35/65 $C_{16}/C_{18}$) oxyethylenated with 15 mol of ethylene oxide, sold under the name Mergital CS 15 by the company Sinnova-Henkel | 3 g |
| Ammonium lauryl sulphate containing 30% of AM | 3.6 g AM |
| Cationic polymer described and prepared according to French Patent FR-2,270,846, or according to U.S. Pat. Nos. 4,217,914, 4,422,853, 4,948,579 and 5,196,189, the disclosures of which are hereby incorporated by reference, consisting of repeat units of formula: | 3 g AM |

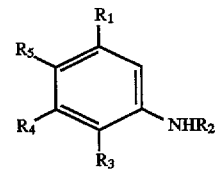

| as an aqueous solution containing 60% of AM | |
|---|---|
| Aqueous ammonia containing 20% of $NH_3$ | 12 g |
| Ammonium thiolactate containing 50% of thiolactic acid | 0.8 g |
| Demineralized water | q.s. for 100 g |

The composition obtained is diluted at the time of use with 1.5 times its weight of 20 volumes hydrogen peroxide, the pH of which is 3.

The mixture thus prepared is applied to natural or permed grey hair containing 90% of white hairs.

The hair is then rinsed, washed with a shampoo and dried.

The colouring that would be obtained is intense coppery blond. The inventors believe that this colouring should have a resistance to perspiration, to light and to shampoos that is comparable with that obtained for the dye of Example 1 in accordance with the invention.

What is claimed is:

1. An oxidation dyeing composition for keratinous fibres, comprising, in a medium appropriate for dyeing, at least one oxidation dye precursor, at least one of said precursors being 3-fluoro-para-aminophenol or an acid addition salt thereof; and at least one coupler compound of formula (I):

$$\text{(I)}$$

in which $R_1$ represents a hydroxyl radical; $R_2$ represents a hydrogen atom, an alkyl or a mono- or polyhydroxyalkyl radical; $R_3$ represents a hydrogen atom, an alkyl, an alkoxy radical or a halogen atom; $R_4$ represents a hydrogen atom; and $R_5$ represents a hydrogen atom, an alkyl, an alkoxy, a mono- or polyhydroxyalkyl or a mono- or polyhydroxyalkoxy radical; and further in which the alkyl or alkoxy radicals may contain from 1 to 4 carbon atoms; the mono- or polyhydroxyalkyl and mono- or polyhydroxyalkoxy radicals may represent alkyl or alkoxy radicals which may contain from 2 to 3 carbon atoms and from 1 to 3 hydroxyl groups; and the halogen atom may be selected from chlorine, fluorine and bromine atoms;

or an acid addition salt thereof; wherein said at least one oxidation dye precursor and said at least one coupler are present in amounts effective to react with an oxidation agent to dye said keratinous fibres.

2. A dyeing composition according to claim 1, wherein the coupler of formula (I) is 5-(β-hydroxyethylamino)-2-methylphenol, 5-amino-2-methylphenol or an acid addition salt thereof.

3. A dyeing composition according to claim 1, wherein the acid addition salt is selected from hydrochlorides, sulphates, hydrobromides and tartrates.

4. A dyeing composition according to claim 1, wherein 3-fluoro-para-aminophenol or its acid addition salt is present in a proportion ranging from approximately 0.005% to 3% by weight with respect to the total weight of the composition and said at least one coupler of formula (I) or its acid addition salt is present in a proportion ranging from approximately 0.001% to 3% by weight with respect to the total weight of the composition.

5. A dyeing composition according to claim 4, wherein 3-fluoro-para-aminophenol or its acid addition salt is present in a proportion ranging from approximately 0.05% to 2% by weight with respect to the total weight of the composition and further wherein said at least one coupler of formula (I) or its acid addition salt is present in a proportion ranging from approximately 0.05% to 2% by weight with respect to the total weight of the composition.

6. A dyeing composition according to claim 1, wherein the keratinous fibres are human keratinous fibres.

7. A dyeing composition according to claim 1, wherein the keratinous fibres are hair.

8. A dyeing composition according to claim 1, which is ready for use, and which further comprises an oxidizing agent and has a pH ranging from 3 to 11.

9. A process for dyeing keratinous fibres, comprising the steps of:
(i) applying to said fibres the dyeing composition according to claim 1; and
(ii) developing the colour of said dyeing composition in an acidic, neutral or alkaline medium by applying an oxidizing agent to said fibres simultaneously with or subsequently to said dyeing composition.

10. A process according to claim 9, wherein said oxidizing agent is added to said dyeing composition at the time of applying in said step (i).

11. A process according to claim 9, wherein said oxidizing agent is separately contained in a composition (B) and is separately applied to said fibres simultaneously with said dyeing composition.

12. A process according to claim 9, wherein said oxidizing agent is separately contained in a composition (B) and separately applied to said fibers subsequent to said application of said dyeing composition.

13. A process according to claim 9, wherein said keratinous fibres are human keratinous fibres.

14. A process according to claim 9, wherein said keratinous fibers are hair.

15. A kit for dyeing keratinous fibres comprising at least two compartments, one of said compartments containing a dyeing composition according to claim 1, and another of said compartments containing a composition (B) containing an oxidizing agent in a medium appropriate for dyeing.

16. A kit according to claim 15, wherein said keratinous fibres are human keratinous fibres.

17. A kit according to claim 15, wherein said keratinous fibres are hair.

18. A process for dyeing keratinous fibres comprising the steps of:
(i) applying to said fibres a dyeing composition according to claim 1, said dyeing composition being obtained from a kit for dyeing keratinous fibres comprising at least two compartments, one of said compartments containing said dyeing composition according to claim 1 and another of said compartments containing a composition (B) containing an oxidizing agent in a medium appropriate for dyeing; and
(ii) developing the colour of said dyeing composition in said medium by applying said oxidizing agent to said fibres simultaneously with or subsequently to said dyeing composition.

19. A process according to claim 18, wherein said oxidizing agent is applied to said fibres simultaneously with said dyeing composition.

20. A process according to claim 18, wherein said oxidizing agent is applied to said fibres subsequently to said dyeing composition.

21. A process according to claim 18, wherein said keratinous fibres are human keratinous fibres.

22. A process according to claim 18, wherein said keratinous fibres are hair.

23. An oxidation dyeing composition for keratinous fibres, comprising, in a medium appropriate for dyeing,
at least one oxidation dye precursor, at least one of said precursors being 3-fluoro-para-aminophenol or an acid addition salt thereof; and
at least one coupler compound of formula (I):

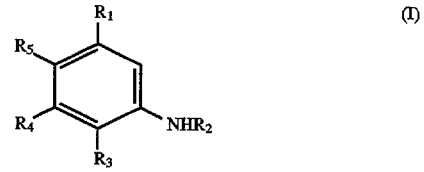

in which $R_1$ represents an amino radical; $R_2$ represents a hydrogen atom, an alkyl or a mono- or polyhydroxyalkyl radical; $R_3$ represents a hydrogen atom, an alkyl or monohydroxyalkoxy radical; $R_4$ represents a hydrogen atom or an alkyl radical; and $R_5$ represents an alkoxy, an aminoalkoxy, a mono- or polyhydroxyalkoxy radical or a 2,4-diaminophenoxyalkoxy radical; and further in which the alkyl or alkoxy radicals may contain from 1 to 4 carbon atoms; and the mono- or polyhydroxyalkyl and mono- or polyhydroxyalkoxy radicals may represent alkyl or alkoxy radicals which may contain from 2 to 3 carbon atoms and from 1 to 3 hydroxyl groups;

or an acid addition salt thereof; wherein said at least one oxidation dye precursor and said at least one coupler are present in amounts effective to react with an oxidation agent to dye said keratinous fibres.

24. A dyeing composition according to claim 23, wherein the coupler of formula (I) is
2,4-diamino-1-(β-hydroxyethyloxy)benzene,
2-amino-4-(β-hydroxyethylamino)-1-methoxybenzene or an acid addition salt thereof.

25. A process for dyeing keratinous fibres, comprising the steps of:
(i) applying to said fibres the dyeing composition according to claim 23; and (ii) developing the colour of said dyeing composition in an acidic, neutral or alkaline medium by applying an oxidizing agent to said fibres simultaneously with or subsequently to said dyeing composition.

26. A kit for dyeing keratinous fibres comprising at least two compartments, one of said compartments containing a dyeing composition according to claim 23, and another of said compartments containing a composition (B) containing an oxidizing agent in a medium appropriate for dyeing.

27. A process for dyeing keratinous fibres comprising the steps of:

(i) applying to said fibres a dyeing composition according to claim 23, said dyeing composition being obtained from a kit for dyeing keratinous fibres comprising at least two compartments, one of said compartments containing said dyeing composition according to claim 23 and another of said compartments containing a composition (B) containing an oxidizing agent in a medium appropriate for dyeing; and (ii) developing the colour of said dyeing composition in said medium by applying said oxidizing agent to said fibres simultaneously with or subsequently to said dyeing composition.

* * * * *